United States Patent [19]

Giwa-Agbomeirele et al.

[11] Patent Number: 5,413,781
[45] Date of Patent: May 9, 1995

[54] ALKYLMETHYLSILOXANES FOR SKIN CARE

[75] Inventors: Patricia Giwa-Agbomeirele; Gary E. Legrow; Regina M. Malczewski, all of Midland, Mich.

[73] Assignee: Dow Corning Corporation, Midland, Mich.

[21] Appl. No.: 131,347

[22] Filed: Oct. 4, 1993

Related U.S. Application Data

[63] Continuation-in-part of Ser. No. 892,838, Jun. 3, 1992, abandoned, which is a continuation of Ser. No. 642,623, Jan. 17, 1991, abandoned.

[51] Int. Cl.$^6$ ............................................. A61K 7/48
[52] U.S. Cl. .................................. 424/78.03; 424/401
[58] Field of Search ................... 424/401, 78.02, 78.03

[56] References Cited

U.S. PATENT DOCUMENTS

| | | | |
|---|---|---|---|
| 4,574,082 | 3/1986 | Tietjen | 424/63 |
| 4,844,826 | 7/1989 | Schaefer et al. | 252/49.6 |
| 4,855,129 | 8/1989 | Steinbach et al. | 424/63 |

OTHER PUBLICATIONS

Cosmetology Society Conf. Apr. 28, 1983 Kollmeier.

*Primary Examiner*—Thurman K. Page
*Assistant Examiner*—Peter F. Kulkosky
*Attorney, Agent, or Firm*—James L. DeCesare

[57] ABSTRACT

A method of treating human skin to decrease transepidermal water loss. A film forming conditioning formulation which includes as an ingredient thereof an organosilicon compound is applied to the skin. The improvement resides in the utilization of a formulation which is dimethylpolysiloxane free and which includes as the organosilicon compound an alkylmethyl polysiloxane.

5 Claims, No Drawings

ALKYLMETHYLSILOXANES FOR SKIN CARE

This application is a continuation-in-part of our prior U.S. application Ser. No. 07/892,838, filed Jun. 3, 1992, now abandoned which is in turn a continuation of U.S. application Ser. No. 07/642,623, filed Jan. 17, 1991, which is now abandoned.

BACKGROUND OF THE INVENTION

This invention relates to personal care and to certain alkylmethyl polysiloxanes useful in skin care applications. More particularly the invention is directed to moisturization and to the formation of films on the skin which function as barriers in order to reduce transepidermal water loss with the result that skin is softened by virtue of its own moisture.

In a recent publication by Th. Goldschmidt AG dated July 1989 and entitled "ABIL ® Silicones" it is reported that certain polysiloxane polyalkylene copolymers known as ABIL ®-WAX 9800 and ABIL ®-WAX 9801 have utility in skin care applications such as day creams, all purpose creams and body lotions. The materials are said to be soluble in cosmetic oils and waxes and to protect against aqueous media when employed in amounts of one to five percent by weight. These materials otherwise known under The Cosmetics, Toiletries and Fragrances Association adopted names of stearyl dimethicone and cetyl dimethicone have the structural formula:

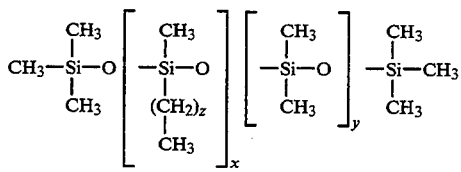

It has been determined by elemental analysis, functional analysis and gel permeation chromatography that the value of the integer x in the above formula is two and that the value of the integer y is four, that is, the ABIL ® siloxanes are low molecular weight. In contrast to these low molecular weight polysiloxanes, the siloxanes of the present invention have a molecular weight upwards of at least ten times the molecular weight of the ABIL ® silicones. As a result the siloxanes of the present invention are less volatile, mope substantive to the skin surface, and form a film on the skin which functions as a barrier to prevent the permeation of moisture upward from the skin and through the film. This reduces the transepidermal water loss from the skin with the result that the skin is softened due to the retention of mope of its own moisture. Test data indicate that the siloxanes of the present invention possess these improved properties to an unexpectedly greater degree than the ABIL ® silicones as will be shown hereinafter.

U.S. Pat. No. 4,574,082 issued Mar. 4, 1986 describes cosmetics containing a dimethylpolysiloxane in admixture with an organopolysiloxane such as polymethyloctylsiloxane and polymethyloctadecylsiloxane. Where these materials are described however they are indicated to be polymers rather than copolymers. In addition, according to the present invention it has been discovered that treatment with a composition that is free of dimethylpolysiloxanes retains mope moisture. This is for the reason that a film of dimethylpolysiloxane allows the permeation of water vapor through the film and therefore dimethylpolysiloxanes suffer from the disadvantage of being ineffective moisture barriers. By eliminating dimethylpolysiloxanes and applying films containing only silicones which are high molecular weight alkylmethylsiloxanes, it has been possible in accordance with the present invention to reduce substantially transepidermal water loss from skin-like collager material due to the presence of dimethylpolysiloxanes and to therefore provide occlusive moisturizing treatments. Such occlusive moisturizing treatments ape not possible with the cosmetic products of the '082 patent.

Protective skin creams are described in United Kingdom Patent No. 737,134 granted Sep. 21, 1955. These skin creams are said to include certain hydrocarbon substituted organosiloxanes. The hydrocarbon radicals are noted preferably to be lower alkyl radicals such as methyl, ethyl and propyl however the British patent indicates that for certain uses higher alkyl radicals such as octadecyl and lauryl radicals may be desired. This description allows the presence of higher alkyl radicals at the ends of the polymer chain rather than along its backbone as in the present invention, and fails to describe copolymeric materials.

Skin care lotions and creams said to include mixed $C_1$-$C_3$ alkyl polysiloxanes such as methylethylpolysiloxane are disclosed in U.S. Pat. No. 4,960,764 issued Oct. 2, 1990. Siloxanes including short chain alkyl groups such as ethyl and propyl do not differ significantly from dimethylpolysiloxanes and therefore the siloxanes of the '764 patent suffer from the disadvantage of being ineffective moisture barriers as explained above in detail. Thus methylethylpolysiloxane and methylpropylpolysiloxane will each possess a high water permeability through their respective film and will each be incapable of functioning as effective occlusive barriers in comparison to the high molecular weight $C_6$ to $C_{30}$ alkylmethylsiloxanes of the present invention. Further short chain alkylmethylpolysiloxanes as described in the '764 patent are less durable and their films may be easily removed from the surface of the skin in contrast to the substantive nature of the films formed by the materials of the present invention.

Accordingly new and novel personal care formulations are provided herein in which an alkylmethyl polysiloxane is utilized as a substantive barrier to water loss to provide soft skin.

SUMMARY OF THE INVENTION

The invention is directed to a method of treating human skin to decrease transepidermal water loss. A film forming conditioning formulation which includes as an ingredient thereof an organosilicon compound is applied to the skin. The improvement resides in the utilization of a formulation which is dimethylpolysiloxane free and which includes as the organosilicon compound an alkylmethyl polysiloxane.

The invention is also directed to personal care and to certain alkylmethyl polysiloxanes useful in skin care applications. Further the invention is related to moisturization and to the formation of films on the skin which function as barriers in order to reduce transepidermal water loss with the result that skin is softened by virtue of its own moisture. In addition the invention includes a method for making the alkylmethyl polysiloxanes and skin care formulations containing alkylmethyl polysiloxanes.

These and other features, objects and advantages of the present invention will be apparent upon consideration of the following detailed description of the invention.

DETAILED DESCRIPTION OF THE INVENTION

In order to treat human skin for the purpose of affecting a decrease in the transepidermal water loss, there is applied to the surface of the skin a dimethylpolysiloxane free film forming conditioning formulation which includes an alkylmethyl polysiloxane having the formula

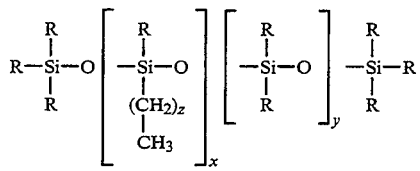

(I)

wherein x and y are integers each of which is equal to at least one and the sum of x and y is from sixty to about one hundred, z is an integer having a value of five to about thirty, and R is an alkyl group having from one to thirty carbon atoms. The alkylmethyl polysiloxane preferably has the formula

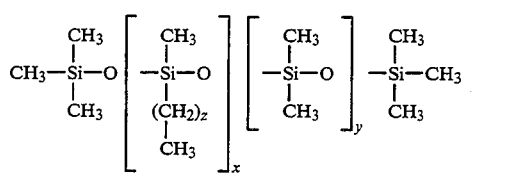

(II)

Most preferred are alkylmethyl polysiloxanes in accordance with the above formula wherein the integer z has a value of five to seventeen.

These materials are produced by the reaction of a linear siloxane having Si-H functionality in the chain such as $(Me_3SiO_{\frac{1}{2}})_2(OSiMeH)_x$ in which Me is methyl and x is forty to the formula $(Me_2SiO)_x$ in which Me is methyl and x is an integer of about three to six preferably four or five. The reaction product is contacted with a slight stoichiometric excess of an alkene $CH_2=CHR$ in the presence of a platinum on carbon catalyst.

Batch production of the alkylmethyl polysiloxanes is conducted by adding the reaction product to a non-agitated suspension of the catalyst in the alkene at about sixty degrees Centigrade. The reaction should be carried out under pressure when the alkene is a short chain alkene smaller than 1-hexene. With longer chain alkenes including 1-hexene and higher the reaction may be conducted at atmospheric pressure.

Continuous production of the alkylmethyl polysiloxanes is conducted by pumping a preheated solution of a five percent stoichiometric excess of an alkene $CH_2=CHR$ and the reaction product through a packed column containing platinum on carbon catalyst chips. The column will require provision for the removal of heat because of the exothermic nature of the reaction.

The materials are further processed in accordance with the present invention in order to provide a more cosmetically acceptable product by removing from the product any remaining cyclic siloxane and any residual methylhydrogendimethylsiloxane cocyclics present as $(MeHSiO)(Me_2SiO)_3$. The alkylmethyl polysiloxanes produced in accordance with the present invention have been found to contain at most about 0.5 percent residual alkene and about 99.5 percent alkylmethyl polysiloxane product. No measurable residual amount of platinum has been detected. The products are otherwise colorless, odorless, non-volatile, clear and stable materials. The products are particularly adapted to skin care in that the materials have been found to form films on the skin which possess a very low water vapor permeability enabling the materials to form a barrier on the skin which will reduce moisture loss from the stratum corneum. The alkylmethyl polysiloxanes find utility in skin creams and lotions including facial products such as cleaners and moisturizers, hand creams, baby creams and sun care creams and lotions.

Of particular utility according to the present invention, are the alkylmethylsiloxnae fluids according to Formula (I), in which the value of the integer x is ten or less, and the value of the integer z is 5 to 17. Where x is ten or less, and z is 5 to 17, the alkylmethylsiloxane fluids of Formula (i) have a viscosity less than about 350 centistokes measured at twenty-five degrees Centigrade. 15 Accordingly, for purposes of the invention, x and y each have a value of at least one. The value of x is ten or less. The sum of x and y is from 60 to 100. The value of z is 5 to 17. These alkylmethylsiloxane fluids have a viscosity of less than about 350 Centistokes.

In order to illustrate the durability of the alkylmethyl polysiloxanes of the present invention in comparison to other materials known in the prior art, data was collected by employing a soap washing procedure that involved the measurement of substantivity on human skin. Materials that were tested included (A) mink oil, (B) an alkylmethyl polysiloxane according to formula (II) but in which the sum of the integers x and y was thirty-five and z was seven, and (C) an alkylmethyl polysiloxane according to formula (II) in which the sum of the integers x and y was between sixty and one hundred and z was seventeen. Sample (C) was a material in accordance with the present invention while Samples (A) and (B) were provided for comparative purposes, Sample (B) was of significantly lower molecular weight than Sample (C). These materials ape identified in the table below as samples (A), (B) and (C) respectively.

Specifically the method was based on Attenuated Total Reflectance/Fourier Transform Infrared Spectrophotometric (ATR/FTIR) analysis in which skin studies were conducted and analyzed based on the reflection of energy at the prism/skin interface. Instrumentation included a NICOLET model 20DX FTIR system and a HARRICK Scientific Skin Analyzer. The ATR studies involved contact of the skin sample and prism. A hydration procedure was employed in order to increase the softness and flexibility of the skin surface which resulted in a less variable contact between the skin and prism. This hydration procedure included placing a water soaked towel against the skin test site for one minute prior to actual spectra collection. A skin test site selected was an area of about eighty square centimeters and about ten to twelve milligrams of each solution tested was applied to the skin test site area in the form of a thin film using a small paint brush. From the data collected it was possible to calculate percentages of ingredients remaining on the skin following various soap wash sequences. The soap employed was a 0.5 weight percent solution of IVORY® bar soap and a soap rub is defined as two passes over the test area with the soap solution cupped in the palm of the hand. One soap wash procedure included fifteen soap rubs and ten rinse rubs under cool running tap water. The test site was the volar forearm. The test solutions were applied to the skin test site on the forearm in the form of a mixture of the test materials dissolved in a hydrocarbon solvent such as ISOPAR®G or a volatile silicone fluid of low viscosity such as polydimethylcyclosiloxane which was a mixture of tetramen and pentamer and having a viscosity of about 2.5 centistokes measured at twenty-five degrees Centigrade. The solution contained five to ten percent by weight of the material in the solvent. The solvent was allowed to evaporate from the volar forearm region for fifteen to thirty minutes prior to the institution of the measurement procedures. The site was hydrated as noted above and the initial spectrum was collected.

A simplified test procedure is illustrated as follows. A test area on the forearm was marked and the test area was washed with the soap solution using fifteen rubs followed by rinsing with ten rubs under cool running water. Excess moisture was blotted from the forearm with a towel. After one minute the skin was hydrated for one minute using a towel saturated with water which was held loosely over the test area. Excess moisture was blotted and at the end of thirty seconds a background scan was run. The text mixture was applied to the skin test area and the solvent allowed to evaporate. The skin was again hydrated for one minute and excess moisture was blotted off. After thirty seconds a scan was run of the test area which represented an Initial Condition. The test area was washed with the soap solution using fifteen rubs followed by ten rinses and the excess moisture was blotted off. After one minute the skin was hydrated for one minute, blotted and at the end of thirty seconds a scan was run of the test area which represented a First Soap Wash Condition. Similar steps were repeated for second, third, fourth and fifth soap wash conditions. Baselines for infrared bands were defined and band heights were measured. The percent ingredient remaining on the skin was calculated using these data.

Table I indicates the results obtained by following the preceding procedure and shows that the alkylmethyl polysiloxane of the present invention as represented by sample (C) is more durable and substantive than prior art materials represented by samples (A) and (B). The alkylmethyl polysiloxanes of the present invention are soap wash resistant and have shown minimal or no dermal irritation.

TABLE I

| | Percent Remaining on Skin After Wash | | |
|---|---|---|---|
| Wash Number | Sample (A) | Sample (B) | Sample (C) |
| 1 | 23 | 34 | 61 |
| 2 | 9 | 24 | 52 |
| 3 | 6 | 18 | 40 |
| 4 | 3 | 12 | 32 |
| 5 | 5 | 10 | 26 |

It should be noted in Table I that the amount of the alkylmethyl polysiloxane (C) of the present invention remaining following the fifth wash was double the amount of Sample (B) which was a low molecular weight alkylmethyl polysiloxane.

The occlusive film forming ability of the alkylmethyl polysiloxanes of the present invention was demonstrated by conducting measurements of transepidermal water loss by employing a Servo-Med Evaporimeter and by skin conductance with a Skicon 200 Skin Surface Hydrometer. The pretreatment rate of water loss was measured at a marked area of the forearm and two drops of the test composition was spread on the marked area of the subject. The composition was allowed to dry and to equilibriate for six hours. The rate of water loss at the treated area and at an area of the forearm which was not treated with the composition was measured. The results of these tests are set forth in Table II below indicating that the alkylmethyl polysiloxanes of the present invention decrease transepidermal water loss by the formation of an occlusive barrier on the skin which retards the rate of penetration of water vapor from the skin through the film.

TABLE II

Transepidermal Water Loss (TEWL) and Conductance Changes in Vivo Following Treatment with Alkylmethyl Polysiloxanes

| | Expressed as $g/m^2h$ | | |
|---|---|---|---|
| Test Number | Sample (A) | Sample (B) | Sample (C) |
| 1 | 3.2 | 2.6 | 2.5 |
| 2 | 3.9 | 1.2 | 2.3 |

In Table II Sample (A) was a control containing no alkylmethyl polysiloxane, Sample (B) was a solvent solution of an alkylmethylpolysiloxane in accordance with the present invention in which the integer z in formula (II) was seven, and Sample (C) was a solvent solution of an alkylmethylpolysiloxane in accordance with the present invention in which the integer z in formula (II) was five.

The test employed to collect data fop Table I was repeated in order to show the improved results obtained by use of the alkylmethylsiloxanes of the present invention (materials I and II) in comparison to the Goldschmidt ABIL® silicone (material IV) mentioned in the "Background" section. A conventional polydimethylsiloxane fluid (material III) was also included for comparative purposes. Table III clearly indicates that the two alkylmethylsiloxanes of the present invention are more durable and substantive than either of the conventional polydimethylsiloxane and the Goldschmidt ABIL® silicone 9800.

ABIL® silicone 9800 is described by the manufacturer as polysiloxane polyalkylene copolymer and The Cosmetics, Fragrance & Toiletries Association adopted name of the material is stearyl dimethicone indicating a value of seventeen fop the integer z in the formula in the "Background" section. The sum of integers x and y is six. ABIL® is a trademark of Th. Goldschmidt AG Chemische Fabriken, Goldschmidtstrasse 100, D-4300 Essen 1, Germany.

TABLE III

| | Percent Remaining on Skin After Wash | | | | |
|---|---|---|---|---|---|
| Material | Wash 1 | Wash 2 | Wash 3 | Wash 4 | Wash 5 |
| I Alkylmethyl siloxane x + y = 100 z = 17 40 mole % z (invention) | 61 | 52 | 40 | 32 | 26 |
| II Alkylmethyl | 79 | 67 | 49 | 46 | 41 |

TABLE III-continued

| Material | Percent Remaining on Skin After Wash | | | | |
|---|---|---|---|---|---|
| | Wash 1 | Wash 2 | Wash 3 | Wash 4 | Wash 5 |
| siloxane $x + y = 100$ $z = 17$ 5 mole % z (invention) | | | | | |
| III Polydimethyl siloxane 500 cs. (comparative) | 22 | 15 | 9 | 0 | 0 |
| IV Alkylmethyl siloxane Goldschmidt ABIL ® 9800 $x + y = 6$ $z = 17$ (prior art and comparative) | 43 | 37 | 24 | 22 | 17 |

The test employed to collect data shown in Table II was repeated in order to compare the alkylmethylsiloxane copolymers of the present invention with U.S. Pat. No. 4,574,082 which teaches mixing polydimethylsiloxanes with certain alkylmethylsiloxanes which are polymers rather than copolymers. Table IV below indicates that when the alkylmethylsiloxane copolymers of the present invention are employed alone and free of dimethylpolysiloxanes, that less water is lost in six hours from a 9.6 square centimeter treated area of collagen film, in comparison to treatment in which the teaching of the '082 patent is followed of mixing a dimethylpolysiloxane and an alkylmethylsiloxane polymer. Thus the "dimethylpolysiloxane free" alkylmethylsiloxane copolymers of the present invention form a more occlusive barrier to water loss than do the materials when mixed with a dimethylpolysiloxane in accordance with the '082 patent.

The term "dimethylpolysiloxane free" as used herein is intended to exclude any linear polydiorganosiloxane which would decrease the barrier capability of the alkylmethylsiloxane copolymers of the present invention in performing their intended function of preventing the escape of water from the skin. The term is not intended to exclude the presence of volatile cyclic siloxanes which may be employed as delivery vehicles and which evaporate leaving little or no residue.

The data presented in Table IV is believed to be fairly representative of the mixtures taught in the 4,574,082 patent. Thus there was employed dimethylpolysiloxanes of ten and five hundred centistokes viscosity as noted in the formulations specified in the '082 patent. In addition the weight percents in Table IV are the same as the weight percents of the '082 patent formulations. In Table IV "PDMS" indicates polydimethylsiloxane.

TABLE IV

| PDMS | | Percent of Alkylmethylsiloxane ($x + y = 100$, $z = 18$, 40 M % z) | Grams Water Lost in Six Hours from 9.6 cm2 test area |
|---|---|---|---|
| Viscosity | Percent | | |
| 500 cs | 25 | 25 | 0.6597 |
| 500 cs | 25 | 5 | 0.7348 |
| 500 cs | 5 | 25 | 0.6208 |
| 500 cs | 100 | 0 | 0.6226 |
| 10 cs | 25 | 25 | 0.6760 |
| 10 cs | 25 | 5 | 0.7335 |
| 10 cs | 5 | 25 | 0.6709 |
| 10 cs | 100 | 0 | 0.6854 |
| — | — | 100 | 0.4824 |
| — | — | 30 | 0.5472 |

Table IV clearly reveals that the occlusivity of the alkylmethylsiloxane copolymers of this invention is reduced by dilution with linear polydimethylsiloxanes since the higher the water loss the less occlusive is the film. Thus in comparison to the teaching of the '082 patent, a new and unexpected result has been discovered herein wherein the alkylmethylsiloxanes of the present invention are applied "free of linear dimethylpolysiloxanes" contrary to the teaching of the '082 patent.

The following example illustrates the method of making the alkylmethylsiloxane copolymers of the present invention.

EXAMPLE

A suspension of 20 grams of Tonsil Optimum FF Clay in a mixture of 1875.2 grams of $(Me_2SiO)_{4\ and\ 5}$ cyclics, 86 grams of $(Me_3SiO(MeHSiO)_{40}SiMe_3)$, and 37.6 grams of 0.65 cs $(Me_3Si)_2O$ was heated at 80 degrees C. and stirred with a magnetic stirrer for 5 hours. During this time samples were taken and the viscosity measured. At the end of the 5 hour period the viscosity became stable at 137 cs. The material was cooled and a clear colorless product was filtered to remove the clay. This product was used as a one thousand gram sample and is referred to as sample I-1.

Sample I-1 was heated at 80 degrees C. at a pressure of 1 mm. with stirring to remove volatile materials, A total of 103 grams of volatile materials were removed leaving 897 grams of a clear colorless liquid of viscosity 184 cs. This material referred to as intermediate I-2. Analytical data were obtained on the intermediate as follows:

| I-2: | % Si—H | 0.0600 |
|---|---|---|
| | GPC | Single narrow dispersity peak |
| | Viscosity | 184 cs. |

To a mixture of 675.3 grams of Intermediate I-2, 119.7 grams of 1-octadecene, and 200 grams of cyclohexane was added 5.0 grams of 0.5% Platinum on Carbon. This mixture was heated at 80 degrees C. for 6 hours under gentle reflux while monitoring the Si-H content. The product had less than 10 ppm Si-H. The product was heated at 110 degrees C. at 1 mm pressure removing 200 grams of volatiles. The composition of the volatiles was cyclohexane. The product was filtered leaving a clear colorless odorless fluid of viscosity 265 cs. This product is referred to as P-2. Analytical data were obtained on the product as follows:

| P-2: | % Si—H - <10 ppm | |
|---|---|---|
| | Platinum - Not Detectable | |
| | GPC - Single narrow dispersity peak | |
| | Viscosity - 265 cs. | |
| | % Non-Volatiles: | >99 |
| | % Volatiles $(Me_2SiO)_{4,5}$ | 0 |
| | $(RMeSiO)_1(Me_2SiO)_{3,4}$ | 0 |
| | Octadecene-1 | <1 |

| |
|---|
| R = 1-Octadecyl |

Toxicity studies were carried out on sample P-2 which showed the sample to have no injurious effects to rabbit skin or eyes.

The viscosity of 265 Centistokes of the product in the above Example is consistent with the preference of the present invention for alkylmethylsiloxane fluids having a viscosity of less than 350 Centistokes.

In addition to the delivery of the alkylmethyl polysiloxanes in the form of solvent solutions, the siloxanes of the present invention may be delivered to the skin in the form of emulsions, microemulsions, solutions, dispersions, lotions, gels, aerosols, solid stick products, ointments or creams.

In addition to the volatile solvent and the alkylmethyl polysiloxane, skin care formulations in accordance with this invention may optionally contain other emollients, sunscreens, and adjuvants such as perfumes, fragrances and preservatives.

Examples of other emollients and moisturizers which may be included in compositions of this invention include straight, branched or cyclic hydroxy compounds such as alcohols containing 1 to 30 carbon atoms; straight, branched or cyclic carboxylic acids containing 1 to 31 carbon atoms, acid esters containing $C_1$ to $C_{30}$ carboxylic acids esterfied with $C_1$ to $C_{30}$ alcohols; alcohol ethers containing 1 to 30 carbon atoms, and alkanes of the formula H—$(CH_2)n$—H wherein n is 5 to 30. Examples of such materials include 2-ethylhexyl oxystearate; arachidyl propionate; 2-ethylhexyl adipate; isopropyl myristate; stearyl alcohol; propylene glycol; propionic acid; stearic acid; polyoxypropylene cetyl alcohol; polyoxypropylene lanolin alcohol; Carbowax * 300; petroleum jelly; mineral oil; aliphatic hydrocarbons such as mineral spirits; lanolin and lanolin derivatives such as acetylated lanolin and isopropyl lanolate.

Sunscreens are evaluated according to their ability to slow the erythema or sunburn resulting from the exposure of skin to ultraviolet light between about 290–320 nanometers (the UV-B region). This is accomplished by absorbing damaging radiation before the radiation contacts the skin surface. Paraaminobenzoic acid derivatives and cinnamates such as octyl methoxycinnamate are examples of preferable and commercially employed categories of sunscreen active compounds. UV-A region agents capable of absorbing ultraviolet light in the range of 320–400 nanometers are also useful in accordance with the present invention including benzophenones and materials such butyl methoxy dibenzoylmethane. Some additional examples of sunscreen chemicals which may be employed in accordance with the present invention are 2-ethoxyethyl p-methoxycinnamate; menthyl anthranilate; homomenthyl salicylate; glyceryl p-aminobenzoate; isobutyl p-aminobenzoate; isoamyl p-dimethylaminobenzoate; 2-hydroxy-4-methoxybenzophenone-5-sulfonic acid; 2,2'-dihydroxy-4-methoxybenzophenone; 2-hydroxy-4-methoxybenzophenone; 4-mono and 4-bis(3-hydroxypropyl)amino isomers of ethyl benzoate; and 2-ethylhexyl p-dimethylaminobenzoate.

As previously indicated, the preferred solvents include aliphatic hydrocarbons such as isoparaffins and volatile cyclic siloxanes. The silicone solvent has the formula $[(CH_3)_2(SiO)]_x$ wherein x is four or five and including mixtures of octamethylcyclotetrasiloxane and decamethylcyclopentasiloxane. Such materials have viscosities of less than five centistokes measured at twenty-five degrees Centigrade. These solvent materials provide a non-cooling and non-stinging solvent like characteristic and evaporate leaving little or no residue. The solvent can also be any aliphatic alcohol such as isopropyl alcohol or ethyl alcohol, esters such as isopropyl myristate and other volatile solvents such as ethyl acetate. It should be noted however that the solvent must be compatible with and capable of dissolving the alkylmethyl polysiloxane as well as any added optional components of the formulation.

The water content of the outer layers of the stratum corneum of human skin is a controlling factor in the appearance of dry skin symptoms. When the stratum corneum contains an adequate amount of water within the range of ten to twenty percent the skin remains flexible. However when the water content falls below ten percent the stratum corneum often becomes brittle and rough and can exhibit scaling and cracking. The stratum corneum receives its water from the deep layers of the epidermis by diffusion or when it is brought into direct contact with water. The diffusion process is controlled by the water content of the skin as well as the concentration gradient. In a very dry environment the water loss from the external skin layers can be significant and often exceeds the rate of replacement by diffusion. An occlusive barrier placed onto the surface of the skin acts to retard the water loss to the environment and allows the skin surface to rehydrate by the diffusion process. Due to the effectiveness and safety of the alkylmethyl polysiloxanes they serve as useful occlusive moisturizers and contribute to dry skin prevention by protection and moisture retention as well as dry skin repair by emolliency, lubricity and moisture restoration.

It should be apparent from the foregoing that many other variations and modifications may be made in the compounds, compositions and methods described herein without departing substantially from the essential features and concepts of the present invention, Accordingly it should be clearly understood that the forms of the invention described herein are exemplary only and are not intended as limitations on the scope of the present invention as defined in the appended claims.

That which is claimed is:

1. A method of forming a film on the skin as a barrier to reduce transepidermal water loss comprising applying a conditioning formulation to the skin which is a polysiloxane copolymer dissolved in a cyclic siloxane, the copolymer having a viscosity of less than about 350 Centistokes, and having the formula

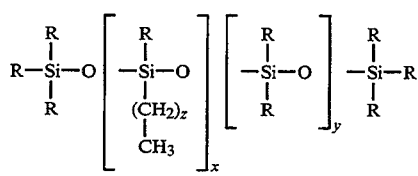

in which x and y are integers each of which is equal to at least one, x has a value of ten or less, the sum of x and y is from sixty to one hundred, z is an integer having a value of five to seventeen, and R is an alkyl group having from one to thirty carbon atoms, the formulation including 5–10 percent by weight of the copolymer in the cyclic siloxane.

2. The method of claim 1 in which the copolymer includes forty mole percent of x units.

3. A film forming conditioning formulation for application to human skin comprising an effective amount of a polysiloxane copolymer dissolved in a cyclic siloxane, the copolymer having a viscosity of less than about 350 Centistokes, and having the formula

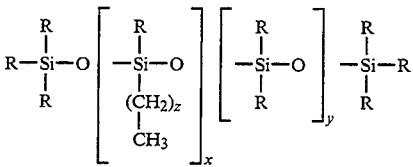

in which x and y are integers each of which is equal to at least one, x has a value of ten or less, and is present in an amount of at least five mole per cent of the total repeating units, and y is present in an amount of units sufficient to provide improved spreading of the material when applied as a film on the skin, the sum of x and y is from sixty to one hundred, z is an integer having a value of five to seventeen, and R is an alkyl group having from one to thirty carbon atoms.

4. The formulation of claim 3 in which the formulation includes 5–10 percent by weight of the copolymer.

5. The formulation of claim 3 in which the copolymer includes forty mole percent of z units.

* * * * *